United States Patent [19]

Kerfoot

[11] Patent Number: 4,804,050
[45] Date of Patent: Feb. 14, 1989

[54] METHOD OF UNDERGROUND FLUID SAMPLING

[75] Inventor: William B. Kerfoot, Falmouth, Mass.

[73] Assignee: K-V Associates, Inc., Falmouth, Mass.

[21] Appl. No.: 44,261

[22] Filed: Apr. 30, 1987

[51] Int. Cl.$^4$ .......................... E21B 49/08; G01N 1/22
[52] U.S. Cl. .................................. 175/20; 73/864.74; 175/21; 175/59
[58] Field of Search ................. 175/21, 20, 59, 60, 175/321, 324, 417, 314; 166/264, 169; 73/864.74, 864.73, 864.64

[56] References Cited

U.S. PATENT DOCUMENTS

| | | | |
|---|---|---|---|
| 2,141,261 | 12/1938 | Clark | 73/864.74 X |
| 3,042,124 | 7/1962 | Anderson | 175/20 |
| 3,084,553 | 4/1963 | Cullinan et al. | 73/864.74 X |
| 3,490,288 | 1/1970 | Patnode | 73/864.74 X |
| 3,835,710 | 9/1974 | Pogorski | 73/864.74 |
| 3,943,750 | 3/1976 | Mc Laughlin | 73/864.74 X |
| 4,261,203 | 4/1981 | Snyder | 73/864.74 |
| 4,310,057 | 1/1982 | Brame | 175/21 |
| 4,335,622 | 6/1982 | Bartz | 175/135 X |
| 4,669,554 | 6/1987 | Cordry | 175/59 |

OTHER PUBLICATIONS

Environmental Affairs Department, "Detection of Hydrocarbons In Groundwater By Analysis of Shallow Live Gas/Vapor", May 1985.

Primary Examiner—Hoang G. Dang
Attorney, Agent, or Firm—Diller, Ramik & Wight

[57] ABSTRACT

A novel apparatus for a method of subsurface sampling which includes a sampling probe having a sample inlet in fluid communication with a sample outlet connected to a tube through which a subsurface medium can be conducted from a desired subsurface point below the earth's surface to a second point thereabove, one of a number of impact sleeves covers the sample inlet, while the sample inlet is covered by the lowermost of the impact sleeves, the probe is driven to a desired subsurface point and during the latter or when the subsurface point is reached, the sample inlet is uncovered thereby creating an uncontaminated flow path for a liquid or vapor sample medium at the desired subsurface point which can be transferred above surface for monitoring-/analyzing. The sample inlets can be selectively uncovered during vertical descent for progressive sensing/analyzing, or alternatively the sample inlets can be themselves surrounded by a slotted impact sleeve to achieve vertical sampling without impact sleeve retraction.

7 Claims, 2 Drawing Sheets

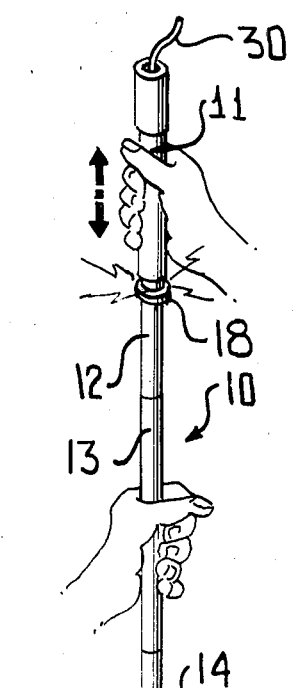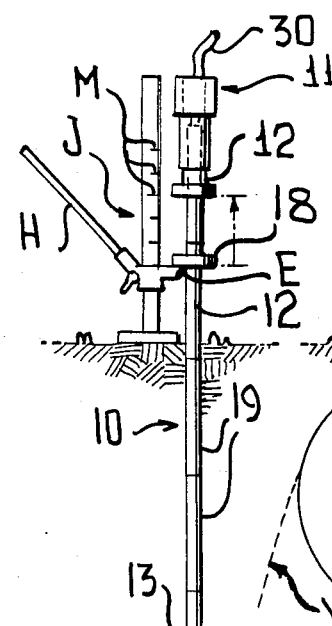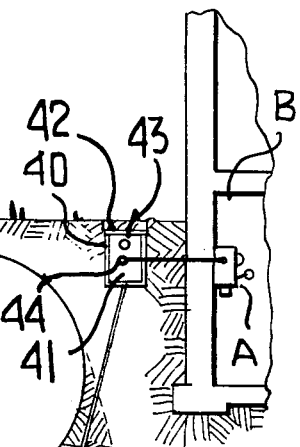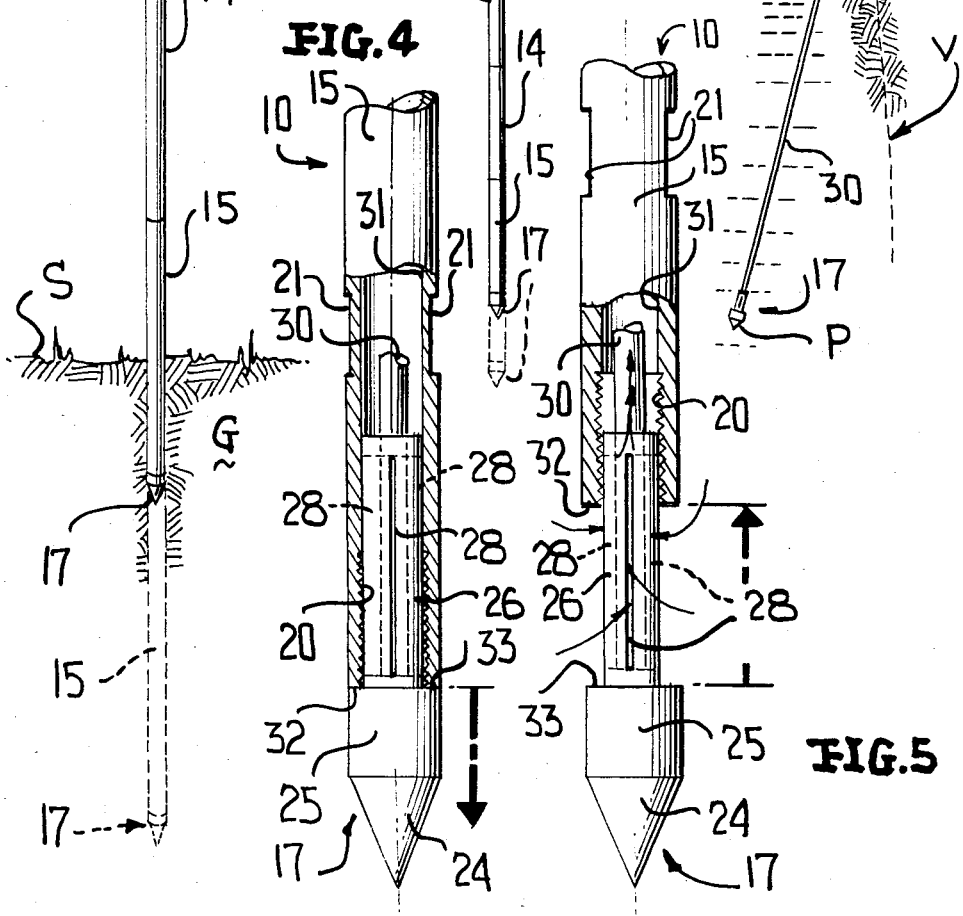

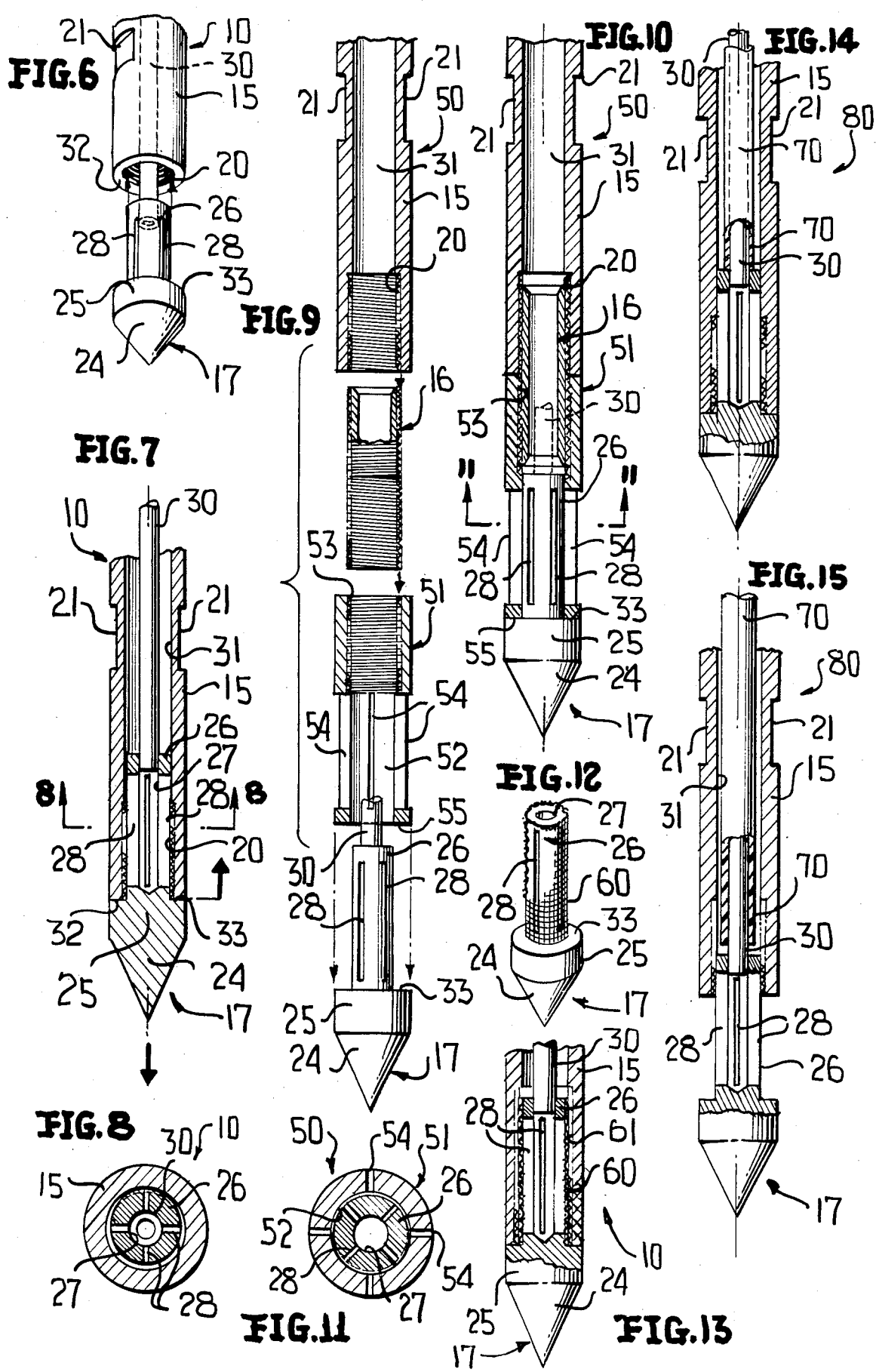

METHOD OF UNDERGROUND FLUID SAMPLING

BACKGROUND OF THE INVENTION

The patentee has for years manufactured, sold and used a well point sampler or ground probe for sampling and analyzing shallow groundwater down to a maximum of approximately ten (10) feet. The well point sampler is used for extracting groundwater samples around lake shores or whatever shallow groundwater exists, and it essentially replaces tedious hand-augering to obtain representative samples of groundwater for water quality analysis.

The well point sampler includes a point threaded to a tubular slotted sleeve (screen), and the latter are connected to lengths of tubing which are driven into the ground to a desired depth. A tube is connected to the screen and to a pump at ground level, and samples of groundwater can thereby be obtained and analyzed. The well point sampler can also be used in this manner in conjunction with a conductivity meter for profiling subsurface plumes.

In recent years the sampling of soil vapors (gasoline, oil and like hydrocarbons) has become extremely important from the standpoint of preventing water quality degradation, inadvertent explosions, etc. The well point sampler is likewise capable of providing vertical profiling of gasoline or oil vapors in the soil by simply connecting the tube to a meter for detecting combustible gases. This can be done at gasoline service stations, for example, to quickly identify the existence of leaking tanks and do so without interruption of service during such testing. Furthermore, as the well point sampler is driven into the ground, readings can be progressively taken and as the probe point descends, high readings caused by surface oil spills would progressively decrease, but at deeper depths the rapid rise of combustible vapors would indicate a region of saturated soil and provide a positive test of leakage from an associated tank.

The fact that soil and groundwater contamination from spills and leaks of petroleum hydrocarbons presents a serious environmental problem is evidence by a recent publication of the American Petroleum Institute of 1220 L Street, N.W., Washington, D.C. 20005 entitled *Detection of Hydrocarbons in Groundwater by Analysis of Shallow Soil Gas/Vapor* which is published by the Environmental Affairs Department, and is identified by API PUBLICATION NO. 4394 of May, 1985. This document represents a consolidation/compilation of a search of open literature relating to subsurface sampling and analyzing techniques, including utilization of ground probes. While driveable ground probes were found to be highly efficient, they tended to be susceptible to "plugging" during insertion, and samples were difficult to obtain in wet, clayey soils. In at least one case a mesh screen was used to prevent blockage of the sample entry holes of the driveable ground probe (See page 44 of the latter publication). Thus, while this publication recognizes driveable ground probes as the preferred types to use for a groundwater contamination investigation, disadvantages noted include the fact that the sample entry ports can become blocked by solid particles and poor results have been obtained for wet, clayey soils (See page 56 of the latter publication).

SUMMARY OF THE INVENTION

In keeping with the foregoing, the present invention is a subsurface sampling system which from an apparatus standpoint includes a sampling probe having a pointed end and a tubular stem provided with one or more sample inlets. A flexible tube is connected to the stem, and a series of impact sleeves are threaded to each other for driving the probe to a desired subsurface point. The most important aspect of the apparatus resides in the fact that the impact sleeve surrounding the slotted stem of the probe covers the sample inlets of the stem during insertion of the probe into the earth, yet the construction is such that the impact sleeve most adjacent the stem can be retracted to uncover the sample inlets not only when a desired final position of the probe is reached, but also during the descent of the probe into the ground. In this fashion the sample inlets are at all times protected and can not become clogged, yet vertical samplings of soil vapor can be achieved with minimal disruption of the overlaying strata. By utilizing a series of vertical and horizontal transects across, for example, a particular suspected spill region and immediately downgrading it one can obtain accurate vertical profiles to define the extent of soil contamination. Furthermore, because of the low costs of the probes and the fact that the impact sleeves can be readily retracted relative to the probes, one or more probes and the associated tubing can be left at desired points below the surface for on-sight continual monitoring.

The same apparatus can also be utilzied in conjunction with a very fine tubular screen or mesh surrounding and covering the sample inlets of the probe stem to additionally decrease the probability of sample inlet clogging.

In keeping with another aspect of this invention the slotted stem of the probe can be covered by the slotted end of an impact tube, preferably with the slots of the latter two components being circumferentially offset from each other, and vertical sampling can take place in a continuous fashion without impact sleeve retraction, as is otherwise necessary in the case of an unslotted impact sleeve most adjacent the sampling probe.

In further accordance with the present invention, another tube preferably surrounds the tube connected to the probe stem to allow air to readily descend downwardly between the two tubes as a vacuum is drawn on the inner tube to effect rapid withdrawal of sample medium.

Because of the inexpensive and virtually expendable nature of the sampling probes/well points of this invention, one, two or any number of sampling probes can be positioned as desired in the soil beneath, for example, in underground fuel oil storage tank which might be monitored to detect future leakage. Of course, if fuel oil has already leaked from the storage tank, this condition would be immediately sensed during the initial sampling as the first sample probe is driven to a desired position relative to the storage tank. However, once the underground storage tank has been located and its boundary determined, the impact sleeves are used to drive several of the sample probes into the ground about the periphery of the storage tank with sensing occuring during descent, as desired. Thereafter, the impact tubes are withdrawn and the tubing from each probe is connected to an appropriate conventional monitor which can be automatically or manually serviced to detect future underground fuel oil/hydrocarbon leakage.

With the above and other objects in view that will hereinafter appear, the nature of the invention will be more clearly understood by reference to the following detailed description, the appended claims and the several views illustrated in the accompanying drawings.

BRIEF DESCRIPTION OF THE DRAWINGS

FIG. 1 is a perspective view of a novel apparatus for subsurface sampling, and illustrates a sampling probing driven into the ground by utilizing a tubular impact hammer and a plurality of interconnected tubular members or impact sleeves.

FIG. 2 is a schematic side elevational view similar to FIG. 1, and illustrates the manner in which the impact sleeves can be partially or totally removed from the ground.

FIG. 3 is a fragmentary schematic vertical sectional view, and illustrates a sampling probe beneath an oil storage tank, and the Teflon tube connecting the sampling probe to conventional monitoring mechanisms to detect vapors which in turn are indicative of storage tank leakage.

FIG. 4 is a fragmentary sectional view of the sampling probe including a point and stem thereof, a plurality of slits or slots in the stem defining sample medium inlets, and a lower end of the lowermost impact sleeve covering the slots to prevent material from clogging/blocking the slots during the driving of the sampling probe into the ground, as shown in FIG. 1.

FIG. 5 is a fragmentary sectional view similar to FIG. 4, and illustrates the lowest impact sleeve being elevated to allow the medium which is to be sampled to be drawn upwardly through the probe slots and the tube at any point desired during the insertion of the sampling probe to obtain progressive vertical sampling of the soil vapor.

FIG. 6 is a fragmentary perspective view of the sampling probe, and illustrates the lower impact sleeve retracted.

FIG. 7 is a fragmentary sectional view of the apparatus of FIG. 4, and more clearly illustrates the sampling slots of the probe stem and the connection of the tube to the stem.

FIG. 8 is a slightly enlarged cross-sectional view taken generally along line 8—8 of FIG. 7, and illustrates details of the impact sleeve, the stem of the sampling probe and the tube.

FIG. 9 is an exploded longitudinal cross-sectional view of the sampling probe. a tubular exterior threaded connector and a pair of impact sleeves, and illustrates the lowest impact sleeve having a plurality of circumferentially spaced slots for shielding or screening the slots of the sampling probe stem.

FIG. 10 is a fragmentary longitudinal sectional view similar to FIG. 9, and illustrates the components thereof in assembled relationship.

FIG. 11 is a cross-sectional view taken generally along line 11—11 of FIG. 10, and illustrates the manner in which the lower slotted impact sleeve surrounds and protects the slots of the sampling probe from being clogged during introduction of the sampling probe into the ground.

FIG. 12 is a perspective view of the sampling probe of this invention, and ilustates a fine mesh screen surrounding the stem.

FIG. 13 is a fragmentary perspective view, and illustrates the sampling probe of FIG. 2, including the screen thereof, received within the end of an impact sleeve.

FIG. 14 is a longitudinal fragmentary cross-sectional view of another apparatus of the invention similar to that of FIGS. 4 through 8, and illustrates another tube in exterior surrounding relationship to the tube connected to the sampling probe stem.

FIG. 15 is a fragmentary longitudinal sectional view of the apparatus of FIG. 14, and illustrates the retraction of the lowermost of the impact sleeves incident to the performance of a sampling operation.

DESCRIPTION OF THE PREFERRED EMBODIMENTS

A novel apparatus for sampling/analyzing subsurface media (liquid or gas) is illustrated in FIGS. 1 and 4 through 8 of the drawings and is generally designated by the reference numeral 10.

The sampling apparatus 10 includes a slidable tubular metallic impact hammer 11; a plurality of metallic tubular members or impacts sleeves 12 through 15 axially connected in adjacent pairs by externally threaded tubular connectors 16 (FIG. 9); and a well point or sampling probe 17, also formed of metallic material.

The impact sleeve 12 has an impact collar 18 welded thereto, and a sacrificial sleeve of somewhat softer metallic material than that of the impact hammer 11 is slid over the impact sleeve 12 above the impact collar 18. Several inches of the sacrificial sleeve project above the upper end (unillustrated) of the impact sleeve 12. The impact hammer 11 is provided with an inner annular shoulder (not shown) which axially opposes the end of the sacrificial sleeve. In order to drive the sampling probe 17 into the ground G from an upper surface S after the apparatus 10 has been assembled, as shown in FIG. 1, the user simply reciprocates the impact hammer 11, as indicated by the unnumbered oppositely directed arrows associated therewith in FIG. 1. During each downward movement, the inner annular shoulder of the impact hammer 11 strikes the upper end of the sacrificial sleeve, and the lower end of the sacrificial sleeve resting upon the impact collar 18 transfers these impact forces downwardly to progressively drive the sampling probe 17 deeper into the ground G. As depth of penetration increases, the impact sleeve 12 is removed, another impact sleeve 19, for example, identical to the sleeves 13 through 15 is added, the impact sleeve 12 is reconnected to the uppermost one of the added impact sleeves 19, and the impact hammer 11 is again continuously reciprocated until the sampling probe 17 is positioned as desired at a predetermined point P (FIG. 3), for example, beneath an existing underground fuel storage tank T for detecting future hydrocarbon/fuel oil leaks, as will be described more fully hereinafter.

The impact sleeves 12 through 15 are secured to each other by simply connecting the externally threaded coupling 16 into internal threads 20 (FIGS. 6 and 9 in particular) at axially opposite ends of each of the impact sleeves 12 through 15. In order to connect and unconnect the impact sleeves 12 through 15, each of the impact sleeves is also provided with diametrically opposite flats or flat surfaces 21, 21 (FIGS. 4 and 9) which can be engaged by an appropriately sized wrench.

The well point or sampling probe 17 is an integral one-piece machined piece of metal (aluminum) having a conical portion or point 24, a cylindrical portion 25, and a tubular stem 26 having an internal axial cylindrical bore 27 and a plurality of relatively narrow slits or slots 28. There are four such slots 28 spaced equally circumferentially about the tubular stem 26. A flexible Teflon tube 30 is tightly fit into the cylindrical bore 27. The exterior diameter of the stem 26 forms a sliding fit with the threads 20 and a cylindrical bore 31 of each of the impact sleeves 12 through 15. An axial annular end face 32 of the lowermost impact sleeve 15 (FIGS. 4 through 6) is in axially opposed relationship to an annular impact shoulder 33 of the sampling probe 17. The slots 28 are approximately 0.010 inch wide and 1.4 inches long, but the width, length and number of slots per sampling probe 17 can be varied depending upon the particular ground G which is to be penetrated, the type of sampling (vapor versus liquid) to be performed, etc.

The apparatus 10 may be employed to avoid future undetected leakage of existing groundwater fuel oil storage tanks T (FIG. 3) through a simple monitoring system by permanently positioning one, two or more sampling probes 17 in the soil/ground G beneath the tank T. The procedure for installation of the sampling probes 17 would first include locating the underground storage tank T after which a pinger or magnetic resonance device can be attached to the tank vent pipe (not shown). An audio wand or magnetic detector can be used to determine the boundary of the buried storage tank T and the boundary can then simply be appropriate marked-off.

With the apparatus 10 assembled, as shown in FIG. 1, including the stem 26 of the sampling probe 17 slidably received in the bore 31 of the lowermost impact sleeve 15 and the opposite end of the tubing 30 projecting outwardly through the upper and of the impact sleeve 12, the tubular sacrificial sleeve (not shown) and the impact hammer 11, the user places the conical point 24 on the surface S (FIG. 3) approximately three feet outside of the marked-off tank boundary. The angle of the apparatus 10 to the vertical is approximately 10 degrees, and the point 24 progressively penetrates the ground G as the impact hammer 11 is continuously reciprocated to drive the sacrificial sleeve against the impact collar 18. In the present example each of the impact sleeves 12 through 15 is approximately 30 inches in length and, obviously, if all were preassembled prior to driving the sampling probe 17 into the ground, it might be necessary to utilize a ladder during the initial stages of the driving operation. However, the apparatus 10 might be first formed only of the sections 12, 15 or 12, 14, 15 to enable a person to simply stand on the surface S adjacent the apparatus 10 and drive the same into the ground without standing on a ladder or the like. In the latter case, as each impact sleeve is driven to a desired depth, the impact sleeve 12 is removed through its coupling 16 from the adjacent impact sleeve to which it is connected, slid off the upper end of the Teflon tube 30, along with the sacrificial sleeve, another impact sleeve (with a coupling 16, if necessary) is then slid on the Teflon tube 30, the latter is connected to the uppermost impact sleeve, and the sacrificial sleeve and impact hammer 11 are then again slid upon the upper end of the Teflon tube 30 with the impact sleeve 12 being connected to the last-added impact sleeve to additionally lengthen the apparatus 10 by another 30 inches. The impact hammer 11 is then reciprocated to impact the sacrificial sleeve against the impact collar 18, and this procedure is repeated until the sampling probe 7 reaches a desired point P (FIG. 3) beneath the tank T within an existing (if the tank T has leaked fuel oil) or a future vapor leakage halo V in the soil or ground G.

At this point the Teflon tube 30 exposed at the upper end of the apparatus 10 can be connected to an appropriate sensor to determine whether explosive vapors V exist beneath the tank T. If explosive vapors V are not detected, a jack J (FIG. 2) having one inch markings M thereon is used to retract the apparatus 10 from the ground G, except for the sampling probe 17 and the tubing 30 retained thereby. The jack J can be, for example, a conventional automobile bumper jack having a lifting end E positioned beneath the impact collar 18 which through the conventional ratchet mechanism and handle H can be used to progressively retract the apparatus 10 and the sections 12 through 15 thereof from the ground G. During the initial retraction operation, it should be particularly noted that due to the sliding fit between the outer surface of the stem 26 and the inner surface 31 and threads 20 of the lowermost impact sleeve 15, the impact sleeve 15 is retracted to expose the slots 28 to the vapors/liquids which are to be sampled. Equally as important is the fact that the lower end portion of the impact sleeve 15 covers the slots 28 during the time the sampling probe 17 is driven into the ground, as is best evident in FIG. 4. Thus, the lower end portion of the impact sleeve 15 defines a covering mechanism or covering means for covering the sample inlets or slots 28 during ground penetration (FIG. 4) while at the same time being further effective for uncovering the sample inlets 28 while the probe 17 is below the surface S thereby creating a flow path for the sample medium at the desired subsurface point P into which the sample medium can flow and/or be drawn by a suitable pump connected to the upper end of the Teflon tube 30. Because the slots 28 are covered until exposed at the desired subsurface sampling point P, samples subsequently taken are totally uncontaminated and, therefore, provide the basis for accurate analysis.

If vapors are detected, the storage tank T might simply be removed, repaired and/or replaced but if there is no vapor detected and future monitoring of the storage tank T is desired, the tubing 30 is connected to an underground conventional manifold 40 having an interior 41 which is closed at its top by a water main housing top 42. Within the manifold 41 are anywhere from one to ten connections to which conventional sampling mechanisms/analyzers can be connected, and two such connections 43, 44 are illustrated for purposes of illustration. If, for example, the storage tank T is to be manually inspected for leakage on a quarterly, semi-annual or annual basis, the inspector would remove the top 42, connect a conventional combustible gas meter to the connector 43 and draw out sampling medium (vapor or liquid) from the point P to determine the existence or nonexistence of vapor. A typical gas meter and suction pump are available from K-V Associates, Inc. of 281 Main Street, Falmouth, Mass. and may be, for example, the "Combustible Gas Meter" disclosed in Data Sheet 11 of May, 1986. Alternatively, if the storage tank T is located adjacent a building B, the connector 44 can be connected by tubing T1 to a conventional vapor/liquid detector/analyzer A which can be manually monitored or which can operate automatically through, for example, an associated timer which would trigger an alarm-/warning light should vapor leakage be detected. The timer could be set for hourly, daily, weekly, monthly or like monitoring periods.

The advantages of the apparatus 10 and the method just described are three-fold, namely, installation can be completed without expensive drilling to groundwater, the Vadose monitoring allows simple sensing installation directly under existing tanks without requiring disruption of service or extensive earth work, and monitoring for leakage can be performed with relatively low-cost explosion meters.

While but a single sampling probe 17 is illustrated beneath the tank T, it is to be understood that additional sampling probes and associated tubing 30 can be positioned at different peripheral locations and/or depths relative to the tank T with the tubing thereof connected to the manifold 40 for conventional analysis.

It is also in keeping with this invention to sample medium in a generally continuous fashion at selective depths during the time the probe 17 is being driven into the ground G for discriminating a leaking tank from surface spills. In the latter case, for example, the impact sleeve 12 could be connected to the impact sleeve 15 and only these two lengths initially used to drive the sampling probes 17 into the ground. After the impact sleeve 15 has been driven its length (approximately 30 inches) into the ground, the jack J could be used to retract the sleeve 15 from the position shown in FIG. 4 to the position shown in FIG. 5 to expose the slots 28, and the height of retraction is readily established/monitored by the marks M (FIG. 2). The retraction should be sufficient to expose the slots 28 but not remove the impact sleeve 15 from the stem 26 of the probe 17. A vapor test at this point might indicate the existence of vapors at the 30 inch level beneath the surface S, but this might simply reflect vapors from oil surface spills, as might be common in gasoline service stations. Thus, the next impact sleeve 14 would be threadedly connected to the impact sleeve 15 and to the impact sleeve 12, and the impact hammer 11 would then be used to drive the sampling probe 17 further into the ground with, of course, the first few inches of downward movement moving the tube 15 from the position shown in FIG. 5 to the position shown in FIG. 4 to once again close the slots 28. After the impact sleeve 14 has been driven virtually its length into the ground G, the sampling probe 17 would be approximately 60 inches below the surface S, and the jack J could be used to retract the apparatus 10 to move the impact sleeve 15 from the position shown in FIG. 4 to that shown in FIG. 5 again exposing the slots 28 to facilitate further sampling. At the 60 inch below surface sampling point it might be found that the vapors have lessened or are nonexistent, and as such testing continues one can readily, rapidly and accurately discriminate the surface spills from tank leakage. Most importantly, all of this testing can be done without contaminating the samples because the slots 28 are covered during descent of the sampling probe 17 and the uncovering (FIG. 5) is limited both in extent and time during vertical testing/analysis.

Another apparatus constructed in accordance with this invention is illustrated in FIGS. 9 through 11 of the drawings and is generally designated by the reference numeral 50. The apparatus 50 is identical to the apparatus 10 except for one additional tubular member or impact sleeve 51 which includes an internal cylindrical bore 52, internal threads 53 and a plurality of generally parallel elongated slits or slots 54. The impact sleeve 51 is at all times located immediately adjacent the sampling probe 17 with an annular end face 55 thereof resting upon the annular impact shoulder 33 of the sampling probe 17, as is best illustrated in FIG. 10. The stem 26 is also freely slidably received within the bore 52 and the threads 53 (FIG. 10) while the coupling 16 connects the impact sleeve 51 to the next impact sleeve 15. The slits or slots 54 can vary in number and are generally 0.019 inch wide and two inches long, but the sizes and numbers of the slots can vary. In an operative apparatus 50 of the present invention, the impact sleeve 51 is provided with eight slots 54, with each slot being 0.019 inch wide and two inches long. The probe 17 associated therewith is provided with six slots 26, each 0.010 inch wide and 1.4 inches long. The stem 26 of the latter-described sampling probe 17 is slid into the bore 52 with, of course, the flexible tubing 30 attached thereto and with no particular concern as to the circumferential orientation of the slots 28, 54 relative to each other (FIG. 11). However, the slots 28, 54 will be in radially opposite relationship when the surfaces 33, 55 are in abutment, as is indicated in FIG. 10. When thus assembled, the apparatus 50 is driven into the ground, just as described earlier with regard to the apparatus 10, but in this case it is unnecessary to axially shift any of the impact sleeves 12 through 15 relative to the probe 17 to vertically sample continuously and progressively as the sampling probe is progressively driven into the ground G. In the present case the slots 54 provide continuous access of vapor/liquid to and into the slots 28 (FIG. 11) and this sampling medium can be continuously monitored through the tubing 30. In this manner the slots 54 generally prevent plugging of the slots 26 and though at times one or more of the slots 54 may themselves become plugged, generally sufficient numbers of the slots 54 remain open during the entire impact insertion of the sampling probe 17 to the point P so that progressive samplings can be made continuously during probe insertion. Obviously, when the sampling probe 17 of FIGS. 9 and 10 had been driven to the point P, the apparatus 50 is removed just as heretofore described relative to FIG. 2, leaving behind only the sampling probe 17 and the tube 30. Thus, in keeping with this embodiment of the invention, the slots 26 are essentially completely covered by the impact sleeve 51 during probe insertion, yet plugging thereof is virtually precluded even though one or more of the slots 54 may become plugged. Thus, when the apparatus 50, including the impact sleeve 51, is retracted, one or more of the slots 28 will be completely opened/unplugged and noncontaminated vapor sampling can be effected at the point P (FIG. 3) in the manner heretofore described.

Reference is now made to FIGS. 12 and 13 of the drawings which illustrates a tubular stainless steel or polyethylene screen 60 a very fine mesh totally encapsulating the stem 26 to additionally prevent clogging of the slots 28 when the impact sleeve 15 has been retracted. If necessary, the bore 31 of the impact tube 15 can be counterbored as at 61 before being threaded to accommodate the additional thickness of the screen 60. However, the screen 60 is so thin that the tolerance otherwise provided between the exterior surface of the stem 26 and the interior surfaces of the threads 20 and bore 31 are sufficent to accommodate the screen 60.

An apparatus 80 of FIGS. 14 and 15 is identical to the apparatus 10 except an exterior flexible Teflon tube 70 is in exterior telescopic relationship to the internal tube 30, the tubes being respectively nominal ¼ inch and 3/16 inch plastic tubing. This arrangement is particularly adapted to withdraw liquid samples from the point P or another point below the surface S by providing an annular air gap of minimum tolerance between the exterior surface of the tube 30 and the interior surface of the tube 70 which reduces the liquid or hydraulic head as vacuum is applied to the end of the Teflon tube 30 above the surface S. Thus, as sample liquid is sucked or drawn into the slots 28, the cylindrical bore 27 and into and up the tube 30, the air between the tubes 30, 70 reduces the head and allows the liquid to be drawn up the tube 30 in a matter of minutes, as opposed to a matter of hours absent the tubing 70. In all other respects the apparatus 80 is identical to the apparatus 10, except, of course, the tube 70 also remains, along with the tube 30, in its in situ implanted position between, for example, the sampling probe 17 of FIG. 3 and the manifold 40.

Although a preferred embodiment of the invention has been specifically illustratated and described herein, it is to be understood that minor variations may be made in the apparatus and the method without departing from the spirit and scope of the invention, as defined in the appended claims.

I claim:

1. A method of subsurface sampling comprising the steps of:
    providing a probe having a sample inlet in fluid communication with a sample outlet in turn in fluid communication with a tube through which a subsurface sample medium can be conducted from a desired subsurface point below earth's surface to a second point thereabove;
    covering the sample inlet;
    inserting the probe with the sample inlet covered into the earth to the desired subsurface point;
    performing the probe inserting step by utilizing at least one tubular member in external telescopic relationship to the tube;
    performing the sample inlet covering step by exteriorly surrounding the sample inlet with a tubular end portion of the tubular member;
    uncovering the sample inlet while the probe is below surface by moving the tubular member and its tubular end portion upwardly thereby creating a flow path for sample medium at the desired subsurface point into the sample inlet to and through the sample outlet and into the tube whereby monitoring of the sample medium can be effected;
    withdrawing the tubular member entirely from the earth while leaving the probe and tube in place; and
    monitoring the sample medium through the tube after the tubular member has been entirely withdrawn from below the earth's surface.

2. The subsurface sampling method as defined in claim 1 wherein the step of inserting is performed by forcefully delivering impact forces against a sacrificial impact tubular member placed against the first-mentioned tubular member to drive the probe through the earth to said second point without damaging said last-mentioned tubular member.

3. The subsurface sampling method as defined in claim 2 including the steps of progressively uncovering the sample inlet during probe insertion at selected points each a different distance below the earth's surface, monitoring the sample medium at each of the selected points, and covering the sample inlet after monitoring the sample medium at each of the selected points and before further probe insertion toward the desired subsurface point.

4. The subsurface sampling method as defined in claim wherein the sample medium monitoring step is performed at selected future time intervals.

5. The subsurface sampling method as defined in claim 1 wherein the sample medium monitoring step is performed continuously.

6. A method of avoiding future undetected leakage of an existing underground storage tank containing a fluid medium comprising the steps of:
    locating an underground storage tank;
    determining the boundary of the storage tank;
    providing a probe having a sample inlet in fluid communication with a sample outlet in turn in fluid communication with a tube through which a subsurface sample medium reflective of storage tank leakage can be conducted from a desired subsurface point adjacent the storage tank to a second point thereabove;
    positioning the probe upon the surface of the earth at a point outboard of the storage tank boundary;
    covering the sample inlet with a tubular end portion of a tubular member;
    driving the probe into the ground to the desired subsurface point;
    performing the probe driving step by placing the tubular member in external telescopic relationship to the tube and against the probe and forcefully driving the tubular member into the ground until the probe is at the desired subsurface point;
    uncovering the sample inlet while the probe is at the desired subsurface point thereby creating a flow path for sample medium at the desired subsurface point into the sample inlet to and through the sample outlet and into the tube;
    performing the probe sample inlet uncovering step by withdrawing the tubular member entirely from the ground while leaving the probe and tube in place; and
    monitoring the sample medium through the tube after the tubular member has been totally withdrawn from the ground.

7. A method of subsurface sampling comprising the steps of:
    providing a probe having a sample inlet in fluid communication with a sample outlet in turn in fluid communication with a tube through which a subsurface sample medium can be conducted from a desired subsurface point below ground surface to a second point thereabove;
    covering the sample inlet with an impact sleeve having a sample inlet of a size to permit flow of sample medium therethrough without extraneous material passage;
    effecting fluid communication between the probe sample inlet and the impact sleeve sample inlet while the probe sample inlet remains covered by the sleeve;
    inserting the probe progressively downwardly below ground surface toward the desired subsurface point while the probe sample inlet is covered by the sleeve; and
    while the probe sample inlet remains covered by the sleeve drawing a subsurface sampling medium into and through the sleeve sample inlet, through the fluid communication means, and into and through the probe sample inlet and outlet and into the tube whereby monitoring of the sample medium can be effected.

* * * * *